(12) United States Patent
Kita

(10) Patent No.: US 8,901,943 B1
(45) Date of Patent: Dec. 2, 2014

(54) GRAVITATIONAL ATTENUATING MATERIAL

(76) Inventor: Ronald J. Kita, Doylestown, PA (US)

( * ) Notice: Subject to any disclaimer, the term of this patent is extended or adjusted under 35 U.S.C. 154(b) by 249 days.

(21) Appl. No.: 13/506,975

(22) Filed: May 29, 2012

Related U.S. Application Data

(63) Continuation-in-part of application No. 12/075,860, filed on May 13, 2008, now abandoned.

(51) Int. Cl.
*G01R 27/26* (2006.01)
*G01N 27/22* (2006.01)

(52) U.S. Cl.
CPC .................. *G01N 27/221* (2013.01)
USPC .......................................... 324/663

(58) Field of Classification Search
CPC ........................................ G01R 27/02
USPC .................. 324/600, 451, 452, 663
See application file for complete search history.

(56) References Cited

U.S. PATENT DOCUMENTS

| | | | |
|---|---|---|---|
| 3,118,022 A | 1/1964 | Sessler | |
| 3,612,778 A * | 10/1971 | Murphy | 381/191 |
| 3,626,605 A | 12/1971 | Wallace | |
| 3,840,748 A * | 10/1974 | Braunlich | 378/122 |
| 4,324,803 A * | 4/1982 | Bergmann et al. | 428/472 |
| 6,493,205 B2 * | 12/2002 | Bauer | 361/245 |
| 6,628,042 B2 * | 9/2003 | Tomohiro | 310/311 |
| 6,960,975 B1 | 11/2005 | Volfson | |

FOREIGN PATENT DOCUMENTS

GB   300311   11/1928

OTHER PUBLICATIONS

Alzofon, F.E AIAA-81 Antigravity, AIAA, New York, NY 1981 p. 3.

* cited by examiner

*Primary Examiner* — Hoai-An D Nguyen

(57) ABSTRACT

A gravitational attenuating material that utilizes an organic based material that has the electrons of the dielectric reconfigured through the use of electrostatic fields, magnetic fields, or photonic or actinic radiation as to render the dielectric less interactive with gravitational forces. The dielectric material is a solid, homo-charged, bipolar binary material having aligned dipoles and made of a polymer and hydrocarbon molecules. Each of the hydrocarbon molecules has at least one aromatic ring and cyclic electron ring current therein. The hydrocarbon molecules are benzene-series molecules, substituted-benzene-series molecules, chloronapthalene molecules, 1,4-dichloronapthalene molecules, chlorobenzene molecules, or 1,2,3-trichlorobenzene molecules.

18 Claims, 5 Drawing Sheets

GRAVITATIONAL ATTENUATING MATERIAL

CROSS REFERENCE RELATED APPLICATIONS

This application is a continuation-in-part of Non-Provisional application Ser. No. 12/075,860, filed May 13, 2008.

FEDERALLY SPONSORED RESEARCH

This invention was made without the support of US Government Funds.

PRIOR ART

| Pat. No. | Code | Issue Date | Inventor |
| --- | --- | --- | --- |
| 3118022 | B1 | Jan. 14, 1964 | Sessler |
| 3626606 | B1 | Dec. 14, 1971 | Wallace |
| 6969975 | B1 | Nov. 1, 2005 | Volfson |
| Foreign Patents: | | | |
| GB 300311 | | Nov. 15, 1928 | Brown |

BACKGROUND OF THE INVENTION

It has been suggested by the research of Podkletnov, Fontana, Tajmar and others that polarized structures such as rf stimulated ceramic superconductors have a reduced interaction with gravity that manifests itself by the reduction of the readings of a scale on which the material rests.

At present, the Dr Eugnevy Podlketnov gravity modification experiment that involved the rotation of a ytterium barium copper oxide superconductors that was rotated at high speed seems not to have been confirmed by other researchers. The large disc approximating 18 inches in diameter had to be isostatically pressed from the aforementioned ceramic material and then must be of sufficient strength to undergo rapid rotation while being subjected to a rf, radio frequency field. Also, the expense that is incurred in the formation of the disc is most substantial as well as being most difficult to form.

According to Nick Cook, Aviation Editor of Janes Defence Weekly, organizations such as NASA as well as Boeing s Project, GRASP, Gravity Research Advanced Space Propulsion Project and British Aerospace, BAe, Project Green Glow has also investigated this technology. Whether their replication was successful or not still remains as an unknown, but many researchers speculate that it was not productive.

Various theories have been proposed as the nature of the operation of the effect produced by such devices. Observations of neutronically polarized metals was first related in a series of gravity modifying patents by Henry Wallace, namely patents U.S. Pat. Nos. 3,626,605 and 3,626,606. Wallace theorized that metals above the atomic number of copper have a higher ratio of neutrons to protons. Lighter metals are usually composed of an equal number of protons and neutrons.

In the case of heavier metals beyond the atomic weight of copper, there is a surplus of neutrons relative to protons and when such metals are placed into such rapid axial rotation, a non-shieldable field similar to a gravitational field is produced. Wallace called this field a kinemassic field or a secondary gravitational field.

The patents of Thomas Townsend Brown and more specifically his patent GB 300,311 reflect that capacitive dielectric materials can influence the interactions between such material and its gravitational attraction when the such materials are subject to high electrical fields.

However over the years, Browns research has been the subject of much criticism, since the effect produced by these high voltages may be interacting with the capacitive material and local objects, thus not representing a true nullification or reduction in the effects that are produced by gravitational forces. The mutual forces produced are merely local repulsive actions.

However, the recent paper by Professor R C Gupta of the University of Luckow, India speculates in his paper: Gravity as a Second Order Manifestation of the Electrostatic Force may represent a true depiction of the nature of gravity. The research paper is available from the Cornell University On-Library: htp://arxiv.org/abs/physics/0505194. It should be noted that Professor Gupta upon meeting the Nobel Prize Laureate, Professor Abdus Salam, who received the 1979 prize in physics, Salam related that Gupta should look for a unification of gravitational with other forces that bear an inverse square relationship. Their meeting was in 1985 during the time that Professor Gupta was at the University of Kenya in Nairobi, and in 2005 the aformentioned paper was published. The Gupta research paper relates: as special relativity provides a link between electric and magnetism in a somewhat similar way it is shown that special relativity provides a much sought after link between electrostatic force and gravitational force.

This area of research appears to be supportive of the research and patents of Brown.

We also should keep in mind as to date that there is no understanding of the nature of the origins of mass, let alone an understanding of gravity. The search for the Higgs Boson, Higgs Particle, at the Large Hardon Collider at CERN-Geneva so far not found such an entity, and even if the Higgs Boson were to be discovered, it would only give an insight into origins of the mass of the electron and other related leptons. As far as arriving at a quantum theory of gravity, Quantum ChromoDynamics Theory or QCD, this would not occur even if the Higgs Boson were discovered.

Also within the field of astrophysics, the concept of repelling or negative gravity has now gained acceptance due to the observations of the mutual accelerations of different galaxies within our universe. In fact, a google search using the descriptors: astrophysics and repulsive gravity will produce over 40,000 hits.

Also in the study with respect to gravity as an electrostatic force, the effect has only been studied in cases where the electrostatic charges were external to the material. It is in the nature of electrostatic forces to form on the surfaces of a substance. For triboelectric energization of a dielectric: as an example, the rubbing of a glass rod with a silk cloth or as in a Van Der Graaf Generator in which a rubber belt is rubbed against a brass collector. The charges that are on the ball-like structure on top of the Van De Graaf Generator are merely represent surface charges, and the same effect holds true for that of the glass rod.

There are few materials in which electrostatic forces are trapped within the material. The most notable is the electret. The term: electret was coined by Sir Oliver Heaviside as the conjunction of two words: electrostatic and magnet. Electrets can be formed from dipolar as well as non-polar molecules. In order to form an electret, dipolar or non-polar molecules are brought to their melting point, then through a series of electrodes the material is polarized by being exposed to a high energy electric field while the material solidifies. In such cases as rosin-carnuaba wax electrets, the material contain trapped electrostatic charges at the interfaces of the two mixed materials as well as experience an alignment of their dipoles.

In the case of 1-chlorobenzene the molecule is intrinsically polar and can be readily polarized by an electrical field. While certain non-polar molecules such a vinyl benzene, styrene, can have an induced dipole moment when such a molecule is subject to high electrical fields. It should be noted that the ordering of such liquid molecules is only temporary, and for modifying a gravitational field a solid structured molecule is more desirable. Also molecules in their liquid state do not have the potential to trap electrostatic charges. In order to trap electrostatic charges the material must change from a liquid into a solid while being subject to an electric field of adequate intensity.

In order to produce a practical electret, the materials must be in solid form. In most cases materials or molecules are heated to their respective melting points, but molecules that are liquid in nature can be polymerized in the presence of an electrostatic and still produce a commercially viable electret, an example of which is styrene.

Electrets should not be confused with ferroelectric materials. Ferroelectric materials in many cases are formed by intrinsic polarization of the material without the need of an electrostatic field. Also, ferroelectrics possess no internal trapped electrostatic field, nor do they manifest an external electric field.

According to Hawley s Condensed Chemical Dictionary, eleventh edition, Ferroelectrics: a crystalline material such as a barium titanate, monobasic potassium-sodium tartrate or Rochelle Salt that over a certain limited temperature ranges has a natural or inherent deformation or polarization of the electric fields or electrons associated with the atoms or molecules in the crystalline lattice. This results in the development of positive and negative poles and a consequent direction of polarization which can be reversed when the crystal is exposed to an external electrical field. With respect to electrets their electrostatic charges are frozen in and do not have the switchable properties as found in ferroelectric materials. Also, a majority of ferroelectrics are formed metallic oxides such as titanates, notably barium titanate or PZT, lead zirconium titanate. Also, the melting point for barium titanate is 3010 F and no known formation of such material into an electret is known.

Electrets in many cases are formed though the use of hydrocarbon-based dielectrics, and in many cases these materials are polymer or natural polymers such as carnuaba wax.

SUMMARY OF INVENTION

Various means of modifying or attenuating the effects of gravity have been tried with little success, such as the use of capacitors or superconductive materials. Research exists into the possibility that gravitation is indirectly related to electrostatics. It is well-known that the laws of gravitation and electrostatics are highly similar, namely they both conform to the inverse square law with respect as to their mutual attraction in decreasing with separation. In fact, if Newton s Law of Gravitation is written relating the proportionality of the respective masses, M and their inverse square relationship, and if M is replaced by Q or charge, the equations are effectively the same.

Also, electrostatic materials that have been heretofore been investigated with respect to their possible gravitational modifying properties have had their electrostatic forces on the surface of the material. In order to modify or attenuate gravitational forces, it is most desirable to have the electrostatic charges within the material itself. For the most part the electrostatic forces that are experienced in our everyday world are surface charges.

Electrets are materials that exhibit in many cases internal charges as well as external or surface charges. Electrets or more specifically electrets that are formed through the use of two materials are called binary electrets. Also by using two dissimilar dielectric materials, the chances of trapping electrostatic charges at interstitial boundaries of the respective materials are effectively increased.

It should be noted that while the effects of a permanent magnet on a ferrous material is readily observable, electrostatic effects as those that are produced by an electret are for the most part, only observable under velocity, acceleration or vibration of the dielectric material. In most cases an electret is indistinguishable from normal materials.

Also, electrets should not be confused with capacitors. Electrets are formed when a dielectric material is taken to its molten state then is polarized through the action of an electric field. Accordingly when the material is allowed to cool the dipole moments are locked in alignment with respect to the electric field, and then depending on the electrochemical nature of the dielectric material subsequent charges may get trapped within certain interstitial or boundary locations. Electrets possess a quasi-permanent electrostatic field, while capacitors have mere transient effects at best, and in most cases, capacitors can be easily permanently discharged.

Also, the polarization of the dielectric materials in the formation of electrets is not limited to dielectrics that are polar in nature or have a dipole moment, but non-polar materials when subject to an electric field while in a molten state can have an induced dipole moment.

The patents of Sessler and Allen relate the polarization of various dielectric materials, and in the patent of Allen atactic polystrene is used. Styrene by its nature does not have a dipole moment, and yet a commercially viable electret is produced. Non-polar materials such as naphthalene have been fabricated into electrets.

It is a goal of this invention to produce a gravitationally modifying or attenuating material that does not rely upon the use of superconductive materials, nor does it have the requirement that such a material be chilled to cyrogenic temperatures to produce an effect.

An object of the invention is to create a gravitational modification or attentuating material that reduces the gravitational attraction of the material and materials contained in the vicinity of the material through the use of an organic material. Organic materials are characterized by the presence of a carbon atom, usually the term organic refers to hydrocarbons. Within the group of such hydrocarbon materials is the benzene-series of molecules.

Benzene was termed as a non-bulk superconductor by Dr Freeman Cope one of the inventors of the MRI, since MRI technology was involved in the study of various possible superconductive materials. Cope investigated numerous cyclic ring current carrying organic materials such as benzene-substituted materials. Benzene due to its conjugate or alternating bond structure evolves ring currents within the molecule. Cope theorized that if the ring currents could be linked, then a bulk superconductor material could be fabricated. Non-bulk superconductors only have non-resistive flows of electrons within the molecule itself. The benzene series of molecules are listed as examples: Benzene, possesses one aromatic ring, naphthalene possesses two aromatic rings and anthracene possesses three aromatic rings. This molecular series continues to higher ring formations.

Benzene series molecules can have their hydrogen atoms substituted, thus rendering them polar. Example, the replacement of one of the hydrogen molecules with a chlorine forms 1-chlorobenzene. Various atoms such as halogens or groups of molcules such as: nitro, carbonyl or hydroxyl groups are examples of substituent molecules.

Organic material have as their advantage over conventional bulk superconductive materials, their relative low cost and ease of fabrication when compared to type 1 and type 2 superconductors.

DESCRIPTION OF THE PREFERRED EMBODIMENT OF INVENTION

Figure 1:
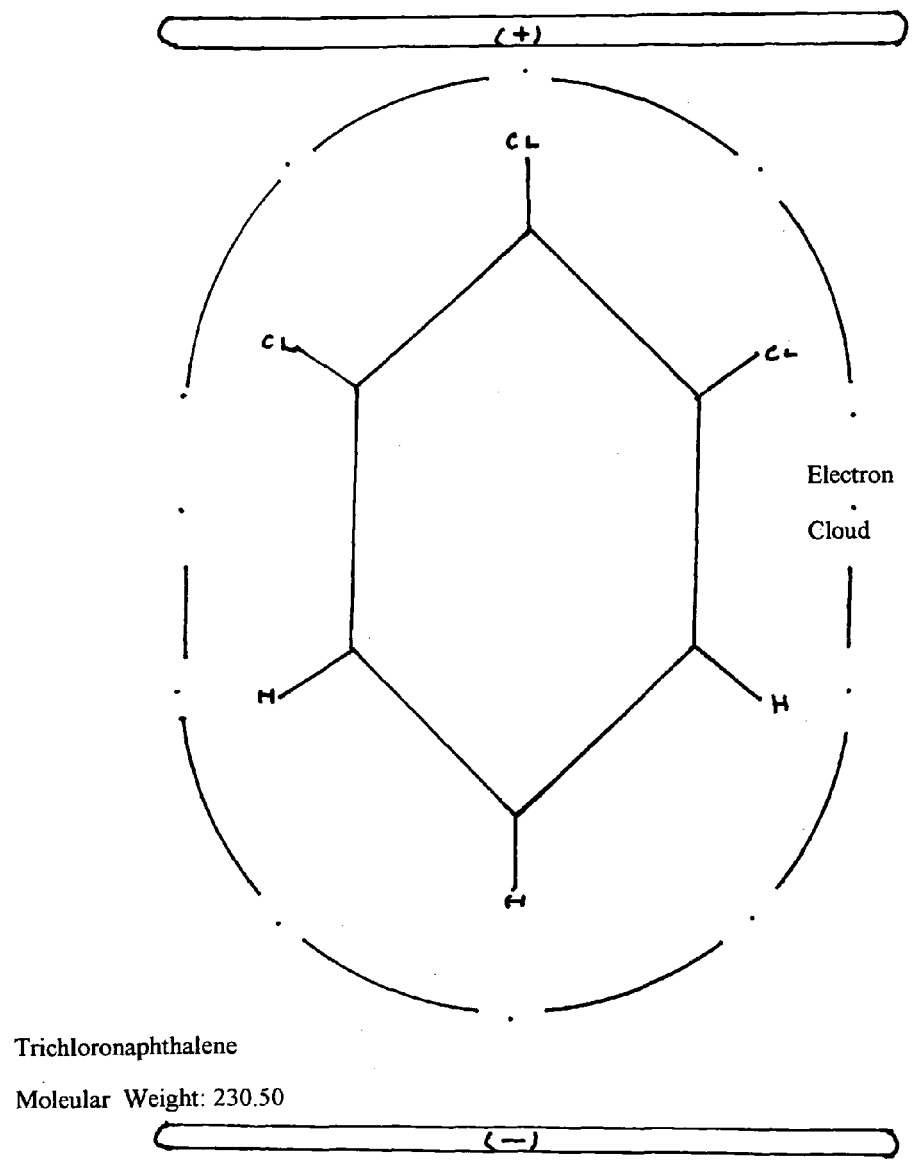
FIG. 1 represents a frontal view of 1,2,3-trichlorobenzene and its electron cloud that is distorted by an electrical field.

The materials used in the fabrication of an electret are largely constituted by materials called dielectrics. Such materials may or may not have an intrinsic dipole moment. However, materials not having a dipole moment can have an induced dipole moment by virtue of placing a suitable electrical stress on the material. In many cases depending on the nature of the molecule an alignment will occur accordingly. In order to achieve such alignment it is desirable to the dielectric in a molten state, since solid molecules are extremely difficult to orientate.

Within the scope of this invention, other polarized materials such as photoelectrets, in which a molten dielectric is subject to photonic source to provide molecular alignment. Radio electrets are electrets that are similarly produced when in a molten state they are exposed to a radio frequency field. Magnetoelectrets are similarly formed through the use of a magnetic field. Thermoelectrets are formed on the melting and cooling of a dielectric while is an electric field, and represent the one of the largest class of electrets.

The concept of a gravito-magnetic electret seems within the realm of possibility since the effects of the action of a magnetic field and gravity has been observed and documented in the research paper by Fujiwara entitled: Magnetic Orientation Under Gravity of BiPhenyl and Naphthalene Crystals.

A list of polar material that are suitable for electret formation, examples include: abietic acid, rosin, trichlorobenzene sucrose, chloronil, dyhydric alcohols, trioxane, camphor, benzophenone, chlorostyrene, chloronapthalene. Of note: in citing the chloronapthalene example, there are liquid forms of substituted benzene and napthalenes molecules.

Example

1-Chlorobenzene is a Liquid that is Polar, but not Desirable for an Electret Material 1,2,3 trichlorobenzene is a polar solid at room temperature and consequently represents a good candidate as an electret material. 1,4-dichloronaphthalene is considered as non-polar, is a solid at room temperature and due to its diamagnetic nature will orientate in a magnetic field. 1,4-dichloronaphthalene can be doped with 2-chloronaphthalene which is polar and the binary dielectric can then be polarized in an electric field. Also, pure 1,4-dichloronaphthalene could attain an induced dipole moment by being exposed to an intense electric field.

In the examples cited above citing the numeric position of the substituted molecule is critical in understanding the dipole nature of the molecule as well as its physical state.

Also, not all trichlorobenzene molecules can be made into a thermoelectret. 1,2,4-trichlorobenzene is a moderately polar liquid at ambient temperatures and is not a solid, hence is not useful.

A list of non-polar material used in electret formation, examples include: polystyrene, carnuaba wax, paraffin, anthracene, naphthalene, phenanthrene, beeswax, polymethacrylate, and other non-substituted aromatic or cyclic molecules.

Of note, the desired'dielectric material can be amorphous or glassy, but crystalline material is preferred. There are 32 crystal classes with 230 space groups, cubic, hexagonal, triagonal, orthorhombic, monoclinic are cited as examples. Of special interest are crystals that belong to the hemihedral and monoclinic groups. In terms of useful compounds, the materials as cited above can be used by themselves or in combinations of the above. Also in the list above there are some molecules that may be polar, but for now they are listed as non-polar. Amorphous non-polar materials are useful in serving as matrixing materials for the containment and orientation of crystals during their alignment by an electric field or other polarizing means. Certain crystals can be aligned by the mechanical action such as rolling of the material. In many situations a polar guest molecule can reside in a non-polar host molecule. In this case the non-polar host constitutes a physical majority of the molecular content.

Figure 2:
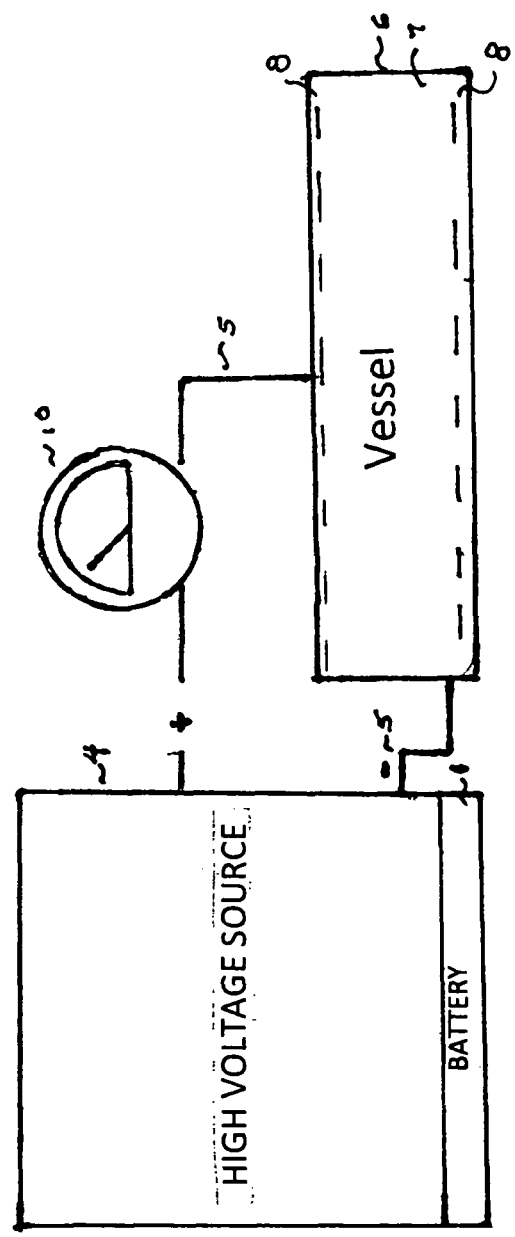
FIG. 2 represents a block diagram of a series of connected electrical devices for the polarization of a dielectric material into an electret.

In FIG. 1 a polar monoclinic molecule, 1,2,3-trichlorobenzene is shown in a distorted state as influenced by being situated between two highly charged plates. In FIG. 2 a block diagram is provided depicting the electrification of the trichlorobenzene that is combined with carnuaba wax, a very slightly polar molecule as compared to the substituted chlorobenzene. Also in FIG. 1, it can be seen that the trichlorobenzene molecular ring current is distorted, since the negative electrons of the electron ring current cloud is drawn toward the positive plate and accordingly the electron ring current is repelled by the negatively charged plate that is located on the opposite side of the molecule. Trichlorobenzene is designated as reference numeral 1, and positive plate as 2, and the negative plate is cited as 3. In FIG. 2 a high voltage power supply 4, through a series of electrical leads 5 feed current vessel 6 containing a molten mixture of a dielectric 7, trichlorobenzene and carnuaba wax. The ratio based upon physical weight is 50% trichlorobenzene and 50% carnuaba wax.

In an electret forming experiment, 50 grams of 1,2,3-trichlorobenzene is mixed with 50 grams of carnuaba wax. The molten mixture was mixed under high illumination in order to determine that the trichloroenzene-carnuaba interface was gone, and that the molten dielectric was now homogeneous. Containment vessel 6 is made from PVC, polyvinylchloride plastic, possessing a diameter of 3.0 inches and possessing a height of 0.5 inches a conductive aluminum mesh is attached to the top of the non-electrically conductive vessel 6 by the means of an adhesive 8. The mesh serves the function as an electroconductive plate 2, while a 3 inch diameter aluminum plate 2 is also attached to the bottom of vessel 6 via an adhesive 8. A power supply, such as those that are utilized in was used as power source 4 photocopying machines. The manufacturer of the aforementioned machine was Nagano Electric of Nagano, Japan Serial Number 8900435 with part no. EK 720552. The output of the device was listed as: 6.4 Kv at 1.2 mA. The input supplied was 24 volts as provided by two 12 volt automotive batteries 9 through a pair of electrical leads 5. The out of the high voltage source was fed through a Shurite milliampere meter 9. The range of the milliampere meter was from 0-10 on the scale. The purpose of the milliampere meter was to monitor the conductivity of the molten dielectric mixture as well as monitoring the progression of the dielectric from the molten state to the non-conductive solidified state.

When the solidified state reaches ambient temperatures an electret is formed, and electrical charges are trapped within the dielectric. Such electrets that are formed by this process are called: homolectret. The term homoelectret is due to the polarity of the material relative to its electrodes. When all electrets are formed: homocharges and hetreocharged electret, the dielectric possesses the oppositete charge of that of the electrotode, but a homocharged electret represents a special case in which a hterocharged electret over time converts to a homocharged electret. In order to achieve this effect that hetre-formed electret must be wrapped in its entirety in a conductive foil 10 then allowed to gradually discharged to zero. After the electretis discharged tozero after usually several days, the charges within the dielectric will rebuild but now they will have the opposite sign. When the reconversion of charges are completed the electret surface charges will be the same or have the same horn-charge as the initial electrodes have. I noted that this charge conversion occurs with the use of electric power. The effect is merely a consequence of the dielectric dipoles reforming.

In the aforementioned experiment the ambient temperature electret was wrapped in its entirety with aluminum foil 10, which was then placed into a polyethylene container 11 as to prevent the effects of humidity from entering the electret. It should be noted that carnauba wax as with most waxes are hydrophobic. Atmospheric moisture should not enter such materials, but since it is matrixed with trichlorobenzene any weight effects to the material must be prevented in order to see the gravity modifying effect as the charges changes. Additionally the container was sealed with a black PVC adhesive tape.

Figure 3:
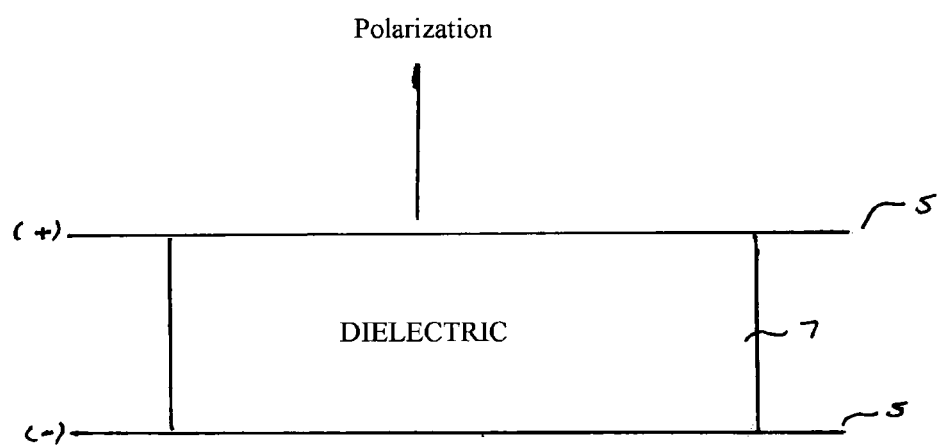
FIG. 3 shows an above view of an electret formed by the apparatus listed above that is enclosed in a conductive foil.
Figure 4:
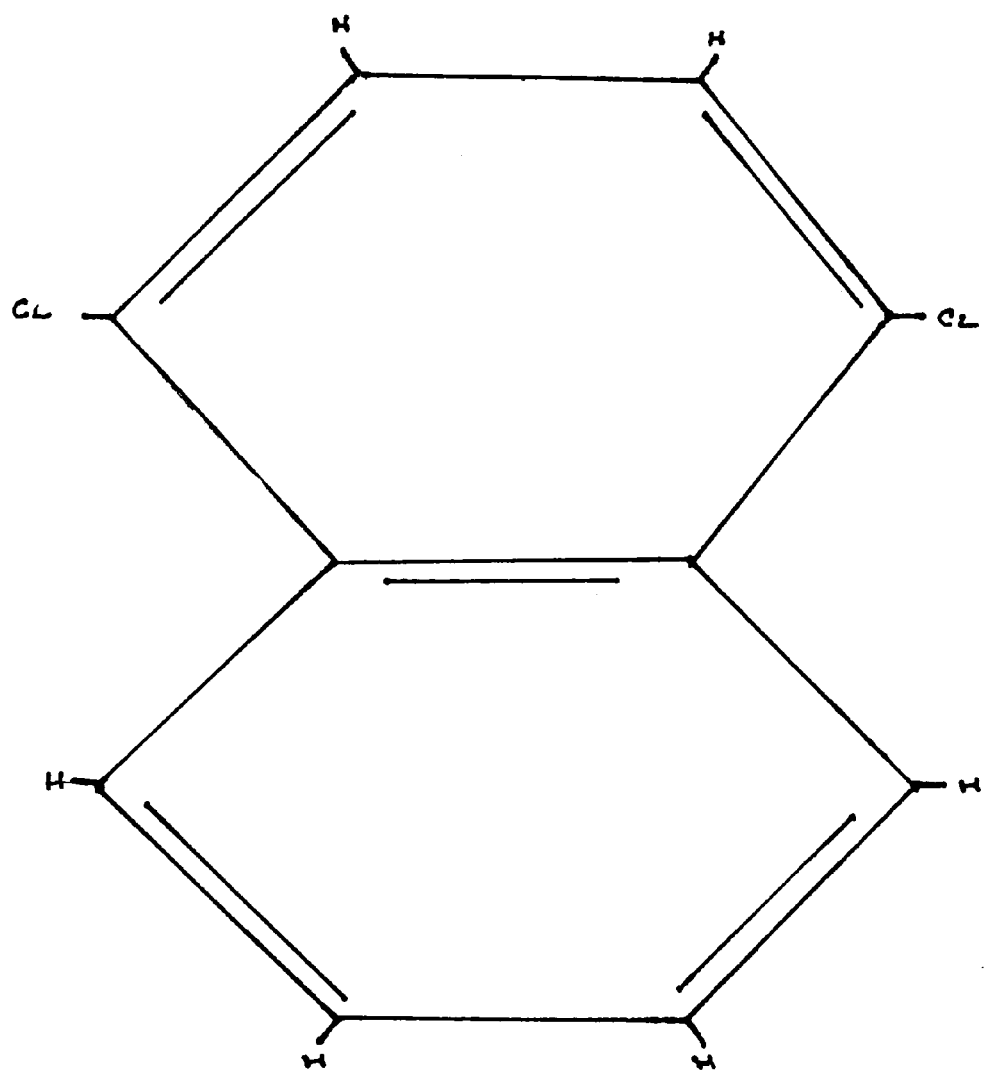
FIG. 4 depicts the frontal view of a 1,4 dichloronaphtalene molecule.
Figure 5:
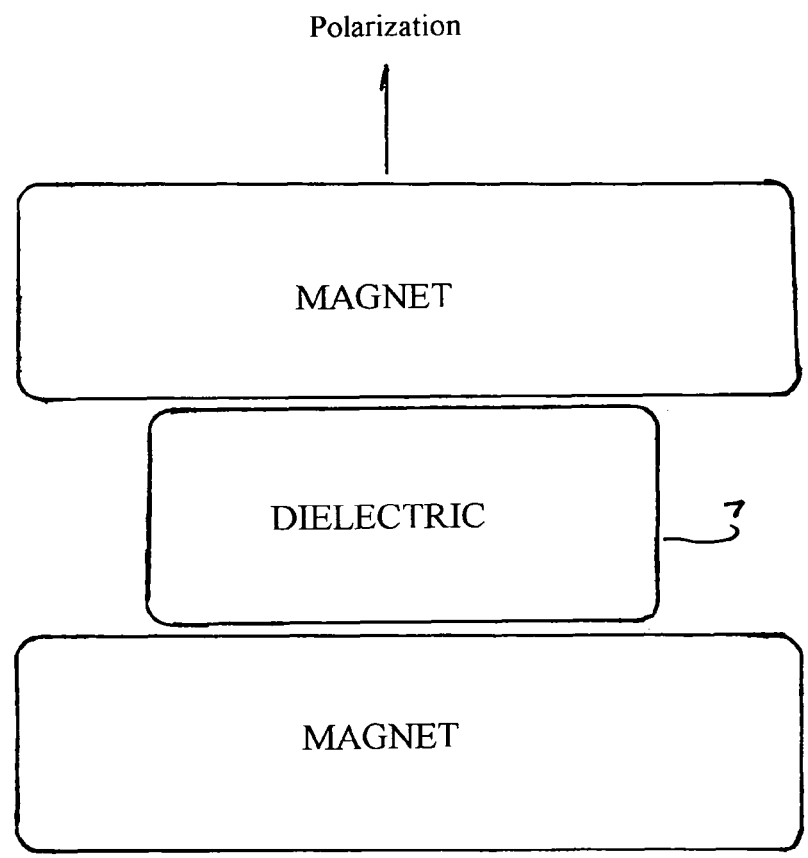
FIG. 5 relates a dielectric polarized by a magnetic field.

The total weight of the electret that was wrapped in the aluminum foil as well as the weight of the PVC tape-sealed container as shown in FIG. 3 was 277.76 grams. A Sargeant-Welch Scale ModelSE-510 with a range limit of 510 grams and possessing an accuracy to 0.01 grams was utilized in the logging of the weight data with respect t time. weight data recordings were taken on a daily basis as the electric charges within the electret discharged to zero. The 277.76 initial weight increased to 277.90 as the charges were neutralized through the electric foil. At this point the electrostatic charges were gone, and weight now was reflective of the actual weight of the dielectric material. The initial 277.76 weight represents the effect that electrostatic molecules has on attenuating the gravitational force that acted on the material.

Also, it should be noted that the discharge of the electret was over 21 days, then the re-establishment and reconversion electrical over the next 21 days, showed a returning of the electret to its initial charge weight and its initial 277.76 grams. During this time period a control mass of the same weight that was placed in a non-electrified condition and was exposed to normal atmospheric humidity, the hydrophobic material experienced no weight change.

Accordingly, the weight changes or the attenuation of gravitational effects occur through the mediation of the electrically charged material. Gravitational attenuation is not the property of all electrets. Also electrets can be fabricated and energized via various polarizing sources such as the examples as cited: electrical fields, magnetic fields, photonic radiation, radio frequency fields, as well as actinic radiation.

The gravitational modifying or attenuation effects as cited are not to be bound by any known theory, but merely seem to suggest that there is a casual relationship between electrostatic charges and gravitational forces.

Also, there are many other embodiments that are envisionable by one skilled in the art, and these specifications are not to be viewed as limiting or restricting.

What is claimed is:

1. A gravitational attenuating material comprising an electrical conductive pair of leads connecting a pair of electrically conductive plates, said plates are connected to a high voltage power source, said plates are connected to a dielectric material via said leads, a containment vessel for the containment of said dielectric material, said dielectric material being a solid, homo-charged, bipolar binary material with aligned dipoles and being made of polymer and hydrocarbon molecules, each of said hydrocarbon molecules having at least one aromatic ring and cyclic electron ring current therein, and said hydrocarbon molecules being selected from a group consisting of benzene-series molecules, substituted-benzene-series molecules, chloronapthalene molecules, 1,4-dichloronapthalene molecules, chlorobenzene molecules, and 1,2,3-trichlorobenzene molecules.

2. The gravitational attenuating material according to claim 1, wherein the hydrocarbon molecules comprise about 50% by weight of the dielectric material.

3. The gravitational attenuating material according to claim 1, wherein the polymer is carnuaba wax.

4. The gravitational attenuating material according to claim 1, wherein the polymer comprises about 50% by weight of the dielectric material.

5. The gravitational attenuating material according to claim 1, wherein the polymer is carnuaba wax and the hydrocarbon molecules are 1,2,3-trichlorobenzene molecules.

6. The gravitational attenuating material according to claim 5, wherein the dielectric material consists of substantially equal parts by weight of the carnuaba wax and the 1,2,3-trichlorobenzene molecules.

7. The gravitational attenuating material according to claim 6, wherein the dielectric material has a thickness of about 0.5 inch.

8. The gravitational attenuating material according to claim 1, wherein the dielectric material has a thickness of no less than 0.5 inch.

9. A gravitational attenuating material, comprising a dielectric material configured to provide a gravity modification effect through the action of the dielectric material having been polarized via electrostatic fields, magnetic fields, or photonic or actinic radiation, said dielectric material being a solid, homo-charged, bipolar binary material with aligned dipoles and being made of a polymer and hydrocarbon molecules, each of said hydrocarbon molecules having at least one aromatic ring and cyclic electron ring current therein, and said hydrocarbon molecules being selected from a group consisting of benzene-series molecules, substituted-benzene-series molecules, chloronapthalene molecules, 1,4-dichloronapthalene molecules, chlorobenzene molecules, and 1,2, 3-trichlorobenzene molecules.

10. The gravitational attenuating material according to claim 9, wherein the polymer is carnuaba wax.

11. The gravitational attenuating material according to claim 9, wherein the polymer comprises about 50% by weight of the dielectric material.

12. The gravitational attenuating material according to claim 9, wherein the polymer is carnuaba wax and the hydrocarbon molecules are 1,2,3-trichlorobenzene molecules.

13. The gravitational attenuating material according to claim 12, wherein the dielectric material consists of substantially equal parts by weight of the carnuaba wax and the 1,2,3-trichlorobenzene molecules.

14. The gravitational attenuating material according to claim 13, wherein the dielectric material has a thickness of about 0.5 inch.

15. The gravitational attenuating material according to claim 9, wherein the dielectric material has a thickness of no less than 0.5 inch.

16. The gravitational attenuating material according to claim 9, wherein the hydrocarbon molecules comprise about 50% by weight of the dielectric material.

17. A method of making a gravitational shielding material, comprising the steps of heating a dielectric material to a molten stated, altering an electron distribution of the dielectric material via use of a magnetic field acting on an electronic structure of said dielectric material, and cooling said dielectric material to a solid state while under the influence of said magnetic field to produce a solid, homo-charged, bipolar binary material having aligned dipoles and being made of a polymer and hydrocarbon molecules, each of said hydrocarbon molecules having at least one aromatic ring and cyclic electron ring current therein, and said hydrocarbon molecules being selected from a group consisting of benzene-series molecules, substituted-benzene-series molecules, chloronapthalene molecules, 1,4-dichloronapthalene molecules, chlorobenzene molecules, and 1,2,3-trichlorobenzene molecules.

18. The method according to claim 17, wherein a permanent magnet is used to provide the magnetic field.

* * * * *